United States Patent
Schneider et al.

(10) Patent No.: US 10,872,474 B2
(45) Date of Patent: Dec. 22, 2020

(54) METHOD AND SYSTEM FOR DYNAMIC ADJUSTMENT OF A MODEL

(71) Applicant: DENTSPLY SIRONA Inc., York, PA (US)

(72) Inventors: Sascha Schneider, Mühltal (DE); Evgenij Derzapf, Lorsch (DE); Ravid Aloni, Gross-Rohrheim (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 16/023,671

(22) Filed: Jun. 29, 2018

(65) Prior Publication Data

US 2020/0005550 A1    Jan. 2, 2020

(51) Int. Cl.
| | |
|---|---|
| *G06T 19/20* | (2011.01) |
| *A61C 7/00* | (2006.01) |
| *A61C 13/34* | (2006.01) |

(52) U.S. Cl.
CPC .............. *G06T 19/20* (2013.01); *A61C 7/002* (2013.01); *A61C 13/34* (2013.01); *G06T 2210/41* (2013.01); *G06T 2219/2012* (2013.01); *G06T 2219/2016* (2013.01); *G06T 2219/2021* (2013.01)

(58) Field of Classification Search
CPC ......... A61C 7/002; G06T 19/20; G06T 17/00; G06T 2207/30036; G06T 19/00; G06T 2219/2004

See application file for complete search history.

(56) References Cited

U.S. PATENT DOCUMENTS

| | | | |
|---|---|---|---|
| 7,705,858 B2 | 4/2010 | Ubillos | |
| 7,746,360 B2 | 6/2010 | Ubillos | |
| 7,760,187 B2 | 7/2010 | Kennedy | |
| 7,889,212 B2 | 2/2011 | Schultz | |
| 8,358,281 B2 | 1/2013 | McCullough | |
| 8,522,158 B2 | 8/2013 | Beck | |
| 9,372,590 B2 | 6/2016 | Zaman | |
| 2008/0077158 A1 | 3/2008 | Haider | |
| 2010/0135543 A1 | 6/2010 | Weese | |
| 2012/0050162 A1* | 3/2012 | Kakuta | ............... G06F 3/011 345/158 |
| 2012/0072177 A1* | 3/2012 | Manai | ............... G06F 17/50 703/1 |
| 2014/0247260 A1 | 9/2014 | Ghoneima | |
| 2015/0135125 A1 | 5/2015 | Bhatt | |
| 2016/0005220 A1 | 1/2016 | Weingarten | |
| 2017/0186222 A1* | 6/2017 | Hata | ............... H04N 5/23219 |

(Continued)

OTHER PUBLICATIONS

International Search Report; PCT/US2019/038938; dated Sep. 24, 2019 (completed); dated Oct. 7, 2019 (mailed).

(Continued)

*Primary Examiner* — Haixia Du
(74) *Attorney, Agent, or Firm* — Dentsply Sirona Inc.

(57) ABSTRACT

A method and system for manipulating a 3D model during treatment planning and automatically adjusting the 3D model based on a localized area of the 3D model proximate to a location of said manipulation. The 3D model is automatically adjusted during the course of treatment planning such that a user has an unobstructed view of the surface. The 3D model may be for example, a 3D model of a tooth or teeth or dental anatomy.

16 Claims, 7 Drawing Sheets

(56) References Cited

U.S. PATENT DOCUMENTS

2018/0045963 A1* 2/2018 Hoover .................. G06F 3/011
2018/0174367 A1* 6/2018 Marom ................ G02B 27/017
2018/0256055 A1* 9/2018 Zigelman ............. A61B 5/0422

OTHER PUBLICATIONS

Written Opinion of the International Searching Authority; PCT/US2019/038938; Sep. 24, 2019 (completed); dated Oct. 7, 2019 (mailed).

* cited by examiner

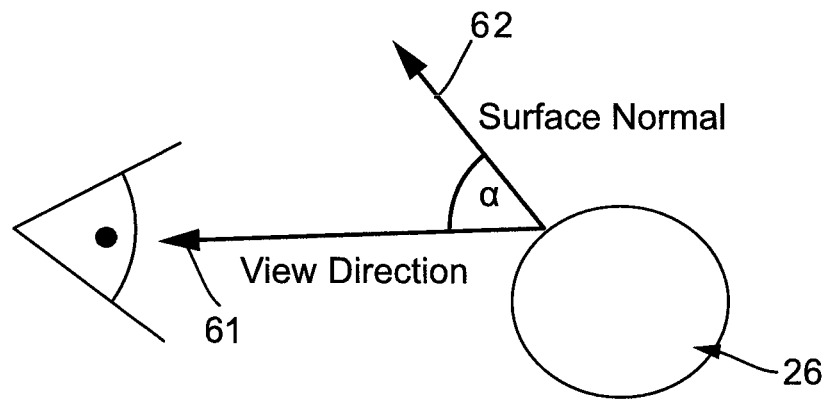
FIG. 6a
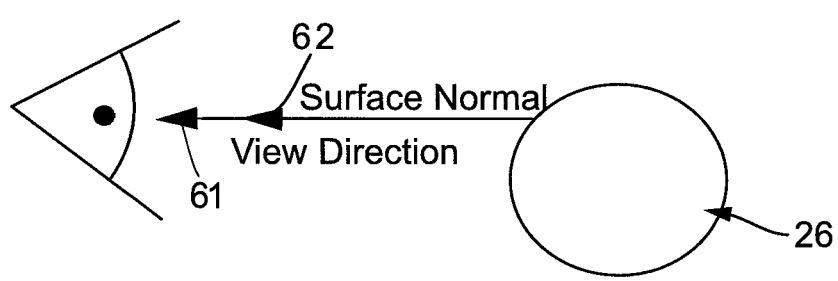
FIG. 6b

METHOD AND SYSTEM FOR DYNAMIC ADJUSTMENT OF A MODEL

FIELD OF THE INVENTION

The present application relates generally to a method for dynamically adjusting model views and, more particularly, to a method and system for dynamically adjusting a view and/or an orientation of a model based on a localized area of the model during treatment planning.

BACKGROUND OF THE INVENTION

Various options exist available for treating dental defects such as by designing restorations or orthodontic aligners. One option is the manual application of filling material in the mouth wherein dentist removes tooth decay and fills a created hole with a filling material. Another option for larger defects includes taking a physical impression by the dentist which may be sent to a dental laboratory to create a plaster model. By taking account of the opposing teeth and, if appropriate, the jaw movements in the form of articulators, it may be possible to produce appropriate tooth restoration or dental prosthetic items such as inlays, onlays, partial crowns, crowns, bridges, telescope crowns, partial prostheses, etc.

However these manual processes are time consuming and expensive. CAD/CAM technology may be an alternative to conventional production methods, in which the dental restorations and dental prosthetic items may be produced with the aid of a computer. Three-dimensional (3D) data may be acquired with hardware such as a dental scanner. A computer-aided design (CAD) data set of a tooth restoration may then be virtually designed or computed using the scanned 3D data and a display. The finished CAD data set may then be machined in a computer-controlled milling or grinding machine (e.g. CNC) or rapid prototyping systems. However designing the virtual restoration is time consuming as the user has to manually change view angles of the restoration during treatment planning in order to have a clear view of a part of the tooth surface being designed.

In one approach, a user may position a pointer over a digital image shown on a screen of a display to cause a magnified view of a portion of the digital image to appear in a box in a fixed location on the screen. This approach may be unfavorable in that the box may cover part of the digital image and the user may need to simultaneously focus on two different areas which may strain the eyes. Moreover such magnified views have only been known to be generated for 2D images.

Further, some text editors may allow a user to change the level of magnification at which a document is being displayed. This approach may be unfavorable because the change of magnification occurs instantaneously, and as a result, the user may become disoriented as to what he or she is viewing after a change in magnification. Further, the entire document may be displayed at the same magnification level, and so it is not possible to view the "big picture" while inspecting a portion of the document at a higher level of magnification. Further, a user may want to modify the document in ways other than just magnification.

U.S. Pat. No. 9,372,590 discloses a magnifier movement system wherein a drag control element is selected for moving a magnifier over a display area.

During dental treatment, a tooth may be scanned prior to preparation, together with the adjacent teeth, and a corresponding 3D model may then be computed.

U.S. Pat. No. 7,705,858 discloses a method and apparatus for displaying digital images on a display wherein a pile of images that include a plurality of images arranged in a first arrangement in which at least one image in the pile overlaps with at least one other image in the pile may be displayed.

U.S. Pat. No. 7,746,360 discloses a method and apparatus for bringing a target region and a correlated visualization together, wherein if the target region is changed, the magnified visualization may be modified as well.

U.S. Pat. No. 7,760,187 discloses a method wherein a region around an area where a user touches the display (touch interaction) may be enlarged.

U.S. Pat. No. 7,889,212 discloses a method and apparatus for enabling selected portions of visual information displayed on a screen to be magnified using a virtual loupe.

SUMMARY OF THE INVENTION

Existing limitations associated with the foregoing, as well as other limitations, can be overcome by methods for dynamically adjusting a 3D model view and/or orientation to generate a 3D model view and/or orientation that is adapted to a surface of the model being worked on. "Dynamic adjustment" of the 3D model may be hereinafter used to mean automatic, continuous and/or intermittent adjustment of a view/visualization/rendering and/or orientation of the 3D model. The model may be any model (for example a 3D model, a 2D model, a stack of 2D models, etc.) and preferably, a 3D model of a tooth or teeth or dental anatomy. For example, 3D model data of a 3D model of teeth may exist in memory and (i) parts of the 3D model data may be left unrendered and/or may be rendered in such a way that the 3D model or parts of the 3D model on a display may appear altered (e.g deleted, made transparent or the like) such that a user may have an optimized view and/or (ii) an orientation of the 3D model may be changed such that a user may have a preferably unobstructed view of the 3D model surface wherein the obstruction may be detected by. For example, determining if a topmost triangle of a tringle mesh of the 3D model in a view direction (said topmost triangle being determined by a buffer containing z coordinates of the 3D model closest to a scanner) is part of a surface being engaged by a user. If said topmost is not part of the surface being engaged, it may be concluded that the surface being engaged is obstructed and the 3D model may be re-oriented.

In an aspect herein, the present invention may provide a method for dynamically adjusting a 3D model, the method comprising the steps of: identifying a 3D model engagement process; obtaining a localized area of the 3D model proximate to a location of the 3D model being worked on; and adjusting the 3D model based on the obtained localized area and the engagement process.

In another aspect herein, any of the aspects of the present invention may be further characterized by one or any combination of the following features: (i) obtaining an orientation of the 3D model based on the localized area; and obtaining a view direction; wherein the adjusting is further based on the obtained orientation and view direction; (ii) adjusting is performed such that the orientation and view direction coincide; (iii) wherein the adjusting is continuous and/or intermittent; (iv) wherein the adjusting includes (a) rotation of the 3D model, (b) translation of the 3D model, (c) magnification of the 3D model or a part of the model, (d) making the 3D model or a part of the model transparent (e) coloring the 3D model or a part of the model; (v) wherein the orientation is based on one or more surface normals or an average of surface normal of the localized area; (vi) wherein the 3D model is a dental model; (vii) wherein the engagement process includes deforming/modifying a surface of the 3D model (viii) wherein the adjusting is further based on a predetermined threshold value; (ix) the predetermined threshold value is an angle formed by (a) one or more surface normals or an average of surface normals of the localized area and (b) a view direction; (x) wherein the adjusting includes a context awareness step wherein an extent of the adjusting, is based on properties of the 3D model; (xi) wherein the properties include tooth structure and/or tooth shape, (xii) wherein the engagement process is a continuous movement of an operator; or (xiii) any combination thereof.

In another aspect, a system may be provided for dynamically adjusting a 3D model, the system comprising: at least one processor configured to: identify a 3D model engagement process; obtain a localized area of the 3D model proximate to a location of the 3D model being worked on; and adjust the 3D model based on the obtained localized area and the engagement process.

In another aspect, any of the aspects of the system may be further characterized by one or any combination of the following features: (i) the processor further configured to; obtain an orientation of the 3D model based on the localized area; and obtain a view direction; wherein the adjusting is further based on the obtained orientation and view direction; (ii) wherein the adjusting is performed such that the orientation and view direction coincide; (iii) wherein the adjusting is continuous and/or intermittent; (iv) wherein the adjusting includes (a) rotation of the 3D model, (b) translation of the 3D model, (c) magnification of the 3D model or a part of the model, (d) making the 3D model or a part of the model transparent (e) coloring the 3D model or a part of the model; (v) wherein the orientation is based on one or more surface normals or an average of surface normals of the localized area; (vi) wherein the 3D model is a dental model; (vii) wherein the engagement process includes deforming a surface of the 3D model; (viii) wherein the adjusting is further based on a predetermined threshold value; (ix) wherein the predetermined threshold value is an angle formed by (i) one or more surface normals or an average of surface normals of the localized area and (ii) a view direction, (x) wherein the adjusting includes a context awareness step wherein an extent of the adjusting, is based on properties of the 3D model; or (xi) any combination thereof.

Dental treatment planning may include designing steps such as drawing marginal lines around tooth and tooth stumps, designing inlays, onlays and partial crowns, implant planning etc. The design steps may be conducted on a display such as the display of a dental CAD/CAM machine. Methods and systems described herein may provide a means for reducing the number of interactions a user needs to complete a treatment planning procedure thereby improving efficiency and reducing treatment planning completion time for example, a method for drawing objects (e.g. lines, circles, curves, irregular shapes or the like) on a 3D model during treatment planning and automatically adjusting a view/orientation of the 3D model based on a localized area of the 3D model proximate to a location of the drawing. This may involve, for example, automatically, continuously and/or intermittently changing an orientation of a three-dimensional (3D) model such as a 3D tooth model, with respect to a view direction (in an embodiment herein being a direction perpendicular to a display plane), when a user interactively engages the model. The orientation may be based on for example one or more surface normals or an average of surface normals. Herein a view angle may be for example an angle between a surface normal of the 3D model and a view direction of the user. The user may therefore be afforded an unobstructed view of a surface of the model being worked on, thus reducing the number of times the user manually changes views of the model to reveal an obstructed surface being worked on. In an embodiment herein, a size of the localized area may range from for example a single point to the surface of a side of a tooth.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein:

FIG. 6*a* illustrates a view direction with respect to a surface normal;

FIG. 6*b* illustrates another view direction with respect to a surface normal;

Figure 1:
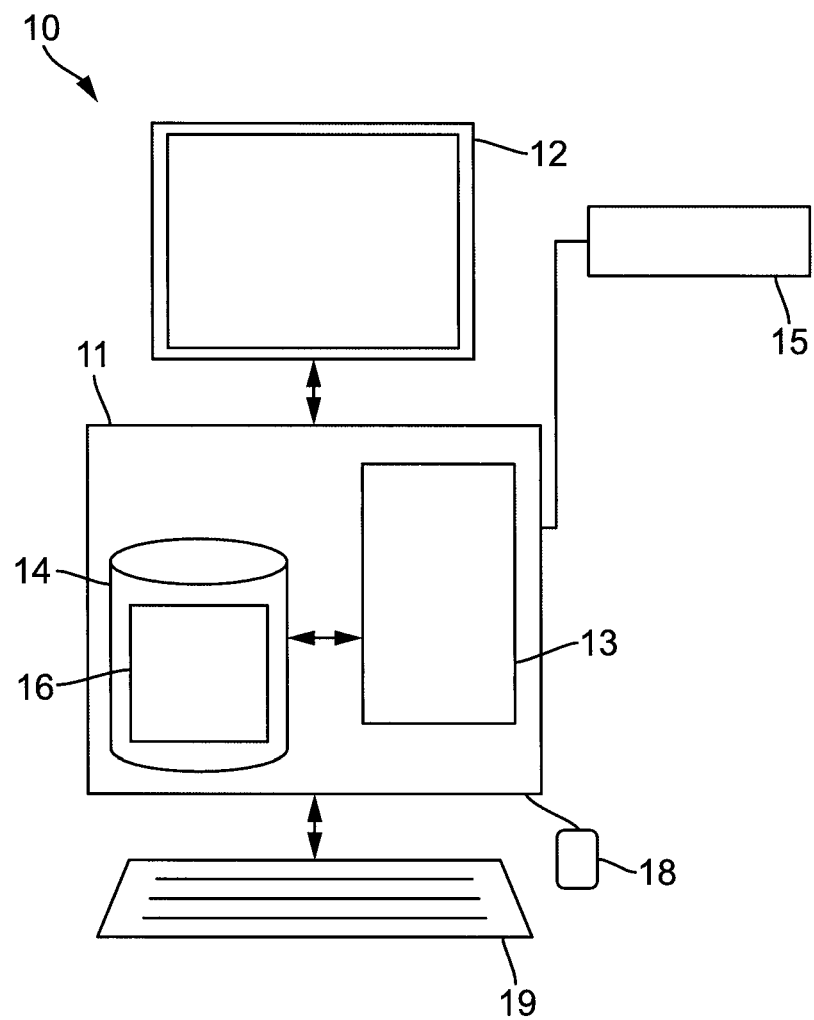
FIG. 1 is a diagram illustrating a system according to an embodiment of the present invention.

Different ones of the Figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method and system may be provided for manipulating a 3D model during treatment planning and automatically adjusting the 3D model view/orientation based on a localized area of the 3D model proximate to a location of said manipulation.

The present invention may provide a method for deforming/modifying (such as altering a shape) a 3D model surface and automatically adjusting an orientation of the 3D model 26 (FIG. 3) based on a localized area of the 3D model 26 proximate to a location of a deformation. Drawing/deformation/interaction tools such as cusp and fissure tools may be employed for drawing on or deforming the 3D model surface prior to adjusting the orientation of the 3D model 26. A threshold value may be used wherein the 3D model view and/or orientation are adjusted after the threshold value is reached. In yet another embodiment herein, the threshold value may include, for example, an angle/angles formed by one or more surface normals 62 (FIG. 6*a*) and a view direction 61. Herein, the one or more surface normals may be dynamically updated as the localized area changes. The adjustment of a view/orientation of the 3D model 26 or a part of the 3D model may include rotation of the model, translation of the model, magnification of the model, coloring the model and/or making the model transparent. The adjustment of the view/orientation of the model may include a context awareness step (step involving the ability to gather information about the dental anatomy at any given time and adapt accordingly) wherein an extent of the adjustment, (including for example speed of rotation/translation and magnification factor), may be dependent on knowledge of properties of the 3D model 26 or properties of part of the 3D model (such as tooth structure and shape).

System for Modeling and Visualizing a Dental Solution

Figure 3:
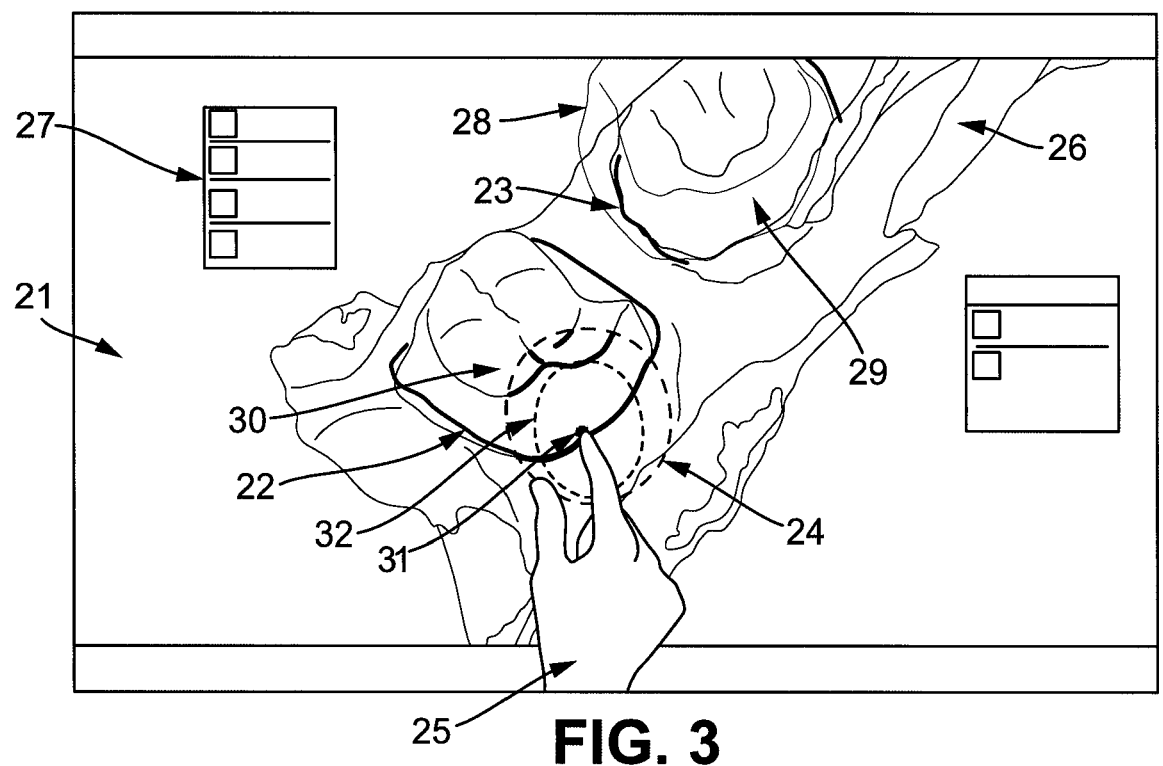
FIG. 3 is a diagram showing a 3D model and tool an embodiment of the present invention.

FIG. 1 illustrates a block diagram of a system 10 comprising a user interface 12 such as graphical user interface, tangible user interface, touchscreen interface 21, gesture driven interface or otherwise user interface that may be used for displaying a model such as a 3D model 26 of a dental anatomy as shown in FIG. 3, and which may be constructed and operated in accordance with at least one example embodiment herein. The user interface 12 may be connected to or form part of a computer system 11. A modeling device 14 having a modeling system 16 may be electrically connected to a processor 13. The modeling device 14 and/or modeling system 16 may form at least part of any of the devices, components, and/or systems discussed herein (for example, as a control circuitry of the user interface 12 to determine and/or translate user input or user gestures (such as touchscreen gestures or touchless gestures), as a handheld controller to detect user movements/gestures and/or as memory or visualization instructions stored in memory for performing visualization steps discussed hereinafter). The processor 13 may be in electrical communication with other components of the computer system 11 or may be part of a different computer system. To execute a procedure, the processor 13 may load appropriate instructions, as stored on a device, into memory and may then execute the loaded instructions.

The system may optionally obtain data for generating the 3D model from an external device 15 such as an optical, laser or x-ray scanner or the system may generate the 3D data from another plurality of 3D data.

The system may include one or more input devices 18, 19, for example, a mouse, a keyboard, a stylus, a trackball, or a natural input such as a finger for drawing on or deforming the 3D model surface.

In one specific embodiment herein, the user interface 12 is preferably a touchscreen interface 21 and the input device 18, 19, is the finger. Herein, the modeling system 16 may detect different operator 25 (finger) gestures on the touchscreen interface 21 and map said detected gestures to corresponding actions as discussed hereinafter. Dynamic adjustment of the 3D model view/orientation may be performed by the processor 13 in tandem with modeling system 16 wherein engagement of the user interface by the operator 25 to draw on or modify a surface 32 of the 3D model 26 may result in initiating the dynamic adjustment to adjust the 3D model according to predetermined criteria as the engagement process (drawing on, deformation of, scaling of, or the like of the 3D model by a user) progresses. Herein manual adjustment (as opposed to dynamic adjustment) of the perspective of the model by the user may be reduced or eliminated such that the user can focus on the design. Instructions for said dynamic adjustment may be controlled by the modeling system 16 and may include but may not be limited to (i) rotation of the model, (ii) translation of the model, (iii) magnification of the model or a part of the model, (iv) making the model or a part of the model transparent (v) coloring the model or a part of the model, (vi) etc. Herein, the 3D model data may exist in memory and a rendering of the 3D model data as seen on the interface 12 may be changed. Said dynamic adjustment may be performed according to criteria which may optionally be set by the user and may include but may not be limited to (i) speed of rotation/translation and (ii) magnification factor of a magnification of a surface 32 of the 3D model. Moreover, the criteria for said dynamic adjustment may optionally be based on context awareness of the 3D model, for example it may be based on properties of the 3D model including but not limited to (i) position/size of adjacent teeth (ii) strength of teeth, (iii) number of restorations needed in the design, (iv) complexity of the design of the restoration, aligner and/or (v) the like etc. It will be appreciated by a person of ordinary skill in the art that similar systems may be achieved for other user interfaces and their corresponding operators 25 according to systems described herein.

Computer System for Modeling and Visualizing a Dental Solution

Having described a system 10 for dynamically adjusting a view/orientation of the 3D model based on a localized area of the 3D model, reference will now be made to FIG. 2, which shows a block diagram of a computer system 100 that may be employed in accordance with at least some of the example embodiments described herein. Although various embodiments may be described herein in terms of this exemplary computer system 100, after reading this description, it may become apparent to a person skilled in the relevant art(s) how to implement the disclosure using other computer systems and/or architectures.

In one example embodiment herein, at least some components of the computer system 100 may form or be included in the computer system 11 of FIG. 1. The computer system 100 may include at least one computer processor 122 and at least one modeling device 150, modeling system 152, user interface 126 and input unit 130 which may form at least part of any of the devices, components, and/or systems discussed herein and/or may respectively form or be included in the processor 13, modeling device 14, modeling system 16, user interface 12 and input device 18, 19 of FIG. 1. The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive an indication that a design is in progress or the 3D model 26 is being engaged and may obtain instructions concerning the dynamic adjustment of the 3D model view/orientation from a memory of the modeling system 152 and/or a from one or more storage units of the computer system 100. The processor 122 may then load the instructions and execute the loaded instructions. This dynamic adjustment of the 3D model view/orientation may then be rendered on the display unit 128.

The user interface (or other output interface) 126 may forward video graphics, text, and other data from the communication infrastructure 124 (or from a frame buffer (not shown)) for display on the display unit 128 (which, in one example embodiment, may form or be included in the display unit 128 of FIG. 1). For example, the user interface 126 may include a video card with a graphics processing unit.

The computer system 100 may also include an input unit 130 that may be used by a user of the computer system 100 to send information to the computer processor 122. In one exemplary embodiment herein, the input unit 130 is a finger or stylus to be used on a touchscreen interface 21. The input unit 130 may alternatively be a trackball or other input device such as a keyboard or stylus or gesture recognition device. In one example, the display unit 128, the input unit 130, and the computer processor 122 may collectively form a user interface 126.

One or more steps of generating the dynamic adjustments may be stored on a non-transitory storage device in the form of computer-readable program instructions. To execute a procedure, the processor 122 loads the appropriate instructions, as stored on a storage device, into memory and then executes the loaded instructions.

Figure 2:
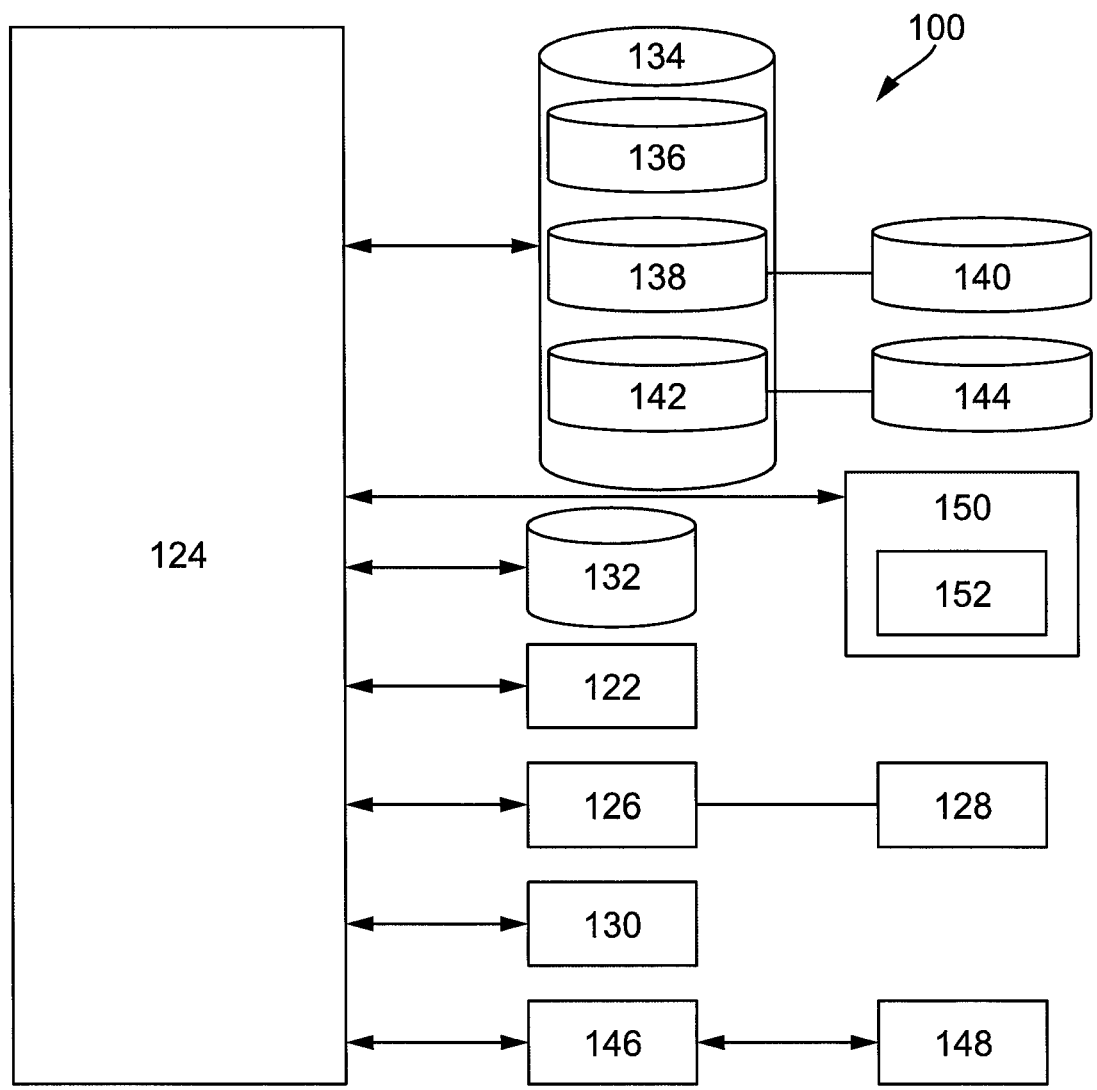
FIG. 2 illustrates a block diagram of an exemplary computer system according to an embodiment of the present invention.

The computer system 100 of FIG. 2 may further comprise a main memory 132, which may be a random access memory ("RAM") and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 carries signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described hereinafter. Accordingly, the computer programs may control the computer system 100 and other components of the systems for modeling and visualizing a dental solution.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for modeling and visualizing a dental solution, to perform all or some of the some of the methods described herein.

Implementation of such other hardware arrangement so as to perform the functions described herein will be apparent to persons skilled in the relevant art(s) in view of this description.

Method for Modeling and Visualizing a Dental Solution.

Figure 7:
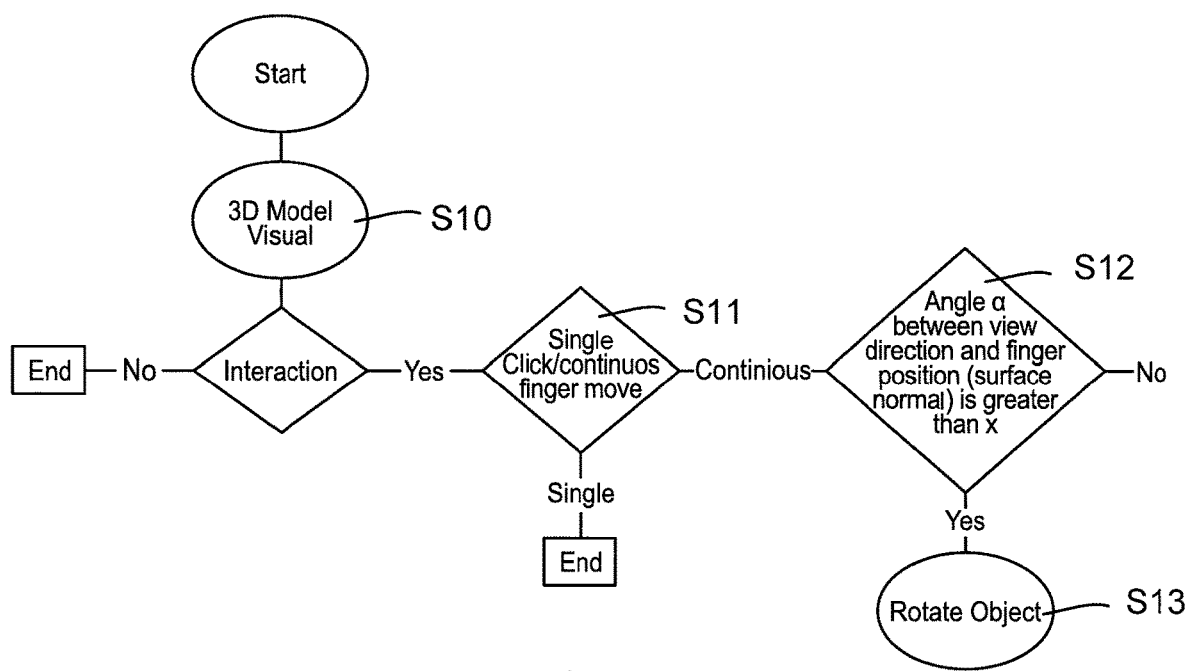
FIG. 7 illustrates an embodiment of a method according to the present invention.
Figure 8:
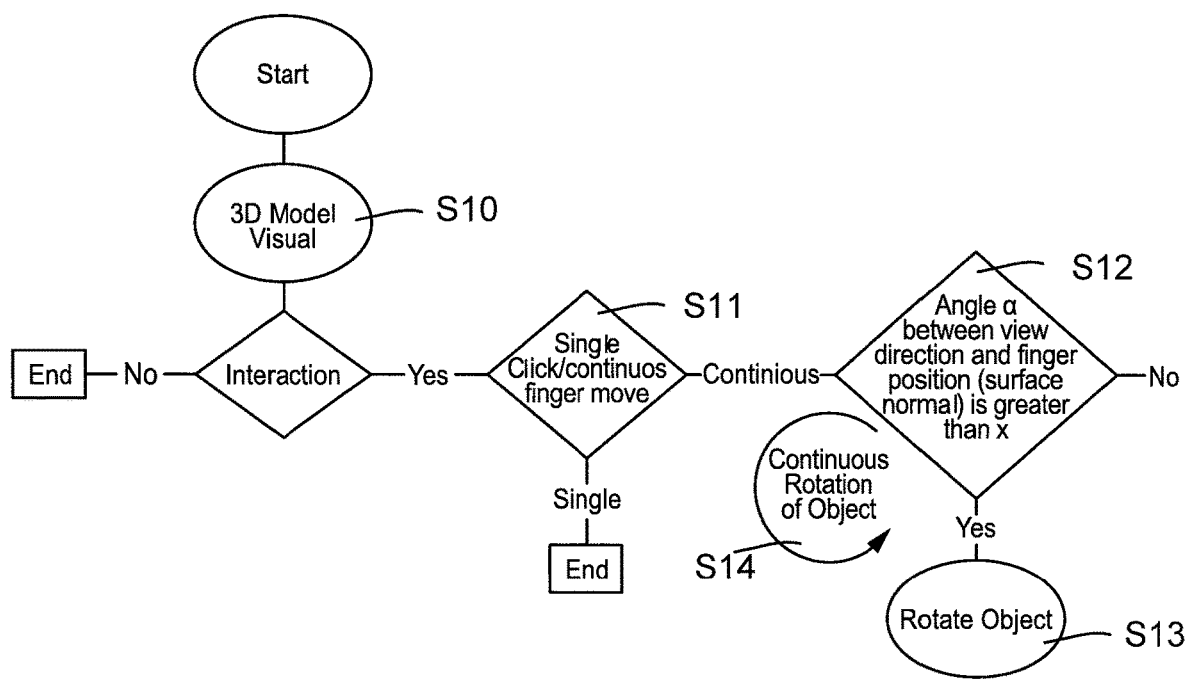
FIG. 8 illustrates another embodiment of a method according to the present invention.

Having described the computer system 100 of FIG. 2, the methods for modeling and visualizing a dental solution 101 will now be further described in conjunction with FIGS. 7-8 which show methods of dynamically adjusting a view and/or orientation of a model based on a localized area of the model during treatment planning.

The invention may include adjusting the 3D model when a user is engaging and/or interacting with (such as moving, placing objects on, drawing on, etc.) a surface 32 or location 31 (such as a point on the 3D model resulting from a click, touch, or otherwise interaction between the user through an input device (or otherwise) and the 3D model) of the 3D model 26. During such interaction, the 3D model 26 may be automatically adjusted with little to no input from the user in a way that may allow the user to have an unobstructed view of the surface 32 being engaged. This adjustment may be based on a localized area of the 3D model proximate to the engagement location/point 31. The adjustment may also preferably be continuous (and optionally automatic) such that the user may have a continuously unobstructed view of any surface 32 being engaged by the user as the design progresses. Herein, the user may have, for example, an orthogonal view of the surface 32 being engaged. Alternatively any parts of the 3D model that may be blocking the surface 32 currently being engaged may be removed or made transparent through 3D rendering methods. Therefore the user may continue designing on and/or modifying the surface 32 without having to stop to manually correct the orientation of the 3D model, because for example, objects moved along the surface 32 shifted out of sight. As the 3D model 26 is dynamically adjusted, the user may save time and the design process may be more efficient.

In an exemplary embodiment of the invention herein, a click or touch of a area on the 3D model may define a location/point 31 or a surface 32 wherein an orientation of the 3D model with respect to a user direction (for example an angle α, as shown in FIG. 6a, between a surface normal 62 of the location/point 31 or an average of surface normals (not shown) of points in the surface 32 with respect to view direction 61) may be calculated. In an exemplary embodiment, the calculation may be achieved by (i) defining a region, for example in $mm^2$ (ii) determining triangles of a triangle mesh in the defined region (iii) computing normal of these triangles (iv) defining a common vector by adding all normal vectors, each multiplied by a surface size of their corresponding triangles (v) and normalizing the common vector (eg. by giving it a length "1"). The orientation of the surface 32 or location/point 31 may then be adapted by for example rotating the 3D object so that the calculated surface normal or average of surface normals fits a direction of the viewer as shown in FIG. 6b.

In another exemplary embodiment herein, drawings such as lines, for example, a first marginal line 22 may be drawn on the 3D model 26. During the drawing of the first marginal line 22 the orientation/view direction on the 3D model 26 may continuously follow the surface normal of the current interaction location/point 31. Herein, during this adaptation/dynamic adjustment of the orientation, one or more surfaces 32 of the current interaction point 31 may be magnified/demagnified to display a magnified/demagnified surface 24 of the one or more surfaces 32. In a similar embodiment, dynamic adjustment of the 3D model view/orientation may be configured to correspond to context awareness of the surface 32 being engaged. For example, anatomically significant areas of the 3D model (such as large curvatures, edges, breaks, holes, teeth cusps, fissures, equator or the like) may be detected through for example mathematical means or through object recognition means and an automatic zoom in/out or view direction adaption of the surface 32 may be initiated, preferably automatically. Moreover the user may slow down or accelerate his design or movement speed on the surface 32 and the automatic zoom in/out or view direction adaption of the surface 32 may be initiated for that surface 32. Furthermore a size of the zoomed area may be adapted to correspond to a resolution or size of the user interface 12. This may guarantee a "real world" dimension of the magnification on the interface 12. Yet still, the magnified/demagnified surface 24 may be steered and/or controlled by the user during the design. Herein gestures such as finger gestures on a touchscreen 21 may be used wherein for example a size of the magnified/demagnified surface 24 or zoom factor may be changed. In a first example, a thumb may be on/outside a border of the magnified/demagnified surface 24 while a 2nd finger may enlarge/shrink the size of the border (area being magnified). In a second example both fingers may be placed within a border of the magnified area to control the zoom factor. In a third example, two fingers may concurrently change the size of the magnifier and the zoom factor. Herein, the user may keep one finger on the touchscreen 21 (e.g. while drawing a line and the magnifier is active). When a second finger is placed on the touchscreen 21, the drawing may be paused to allow the magnifier and its zoom factor to be controlled. Implementation of the same or other gestures in the same or other user interfaces 12 so as to perform the same or similar functions described herein will be apparent to persons or ordinary skill in the relevant art(s) in view of this description.

Figure 4:
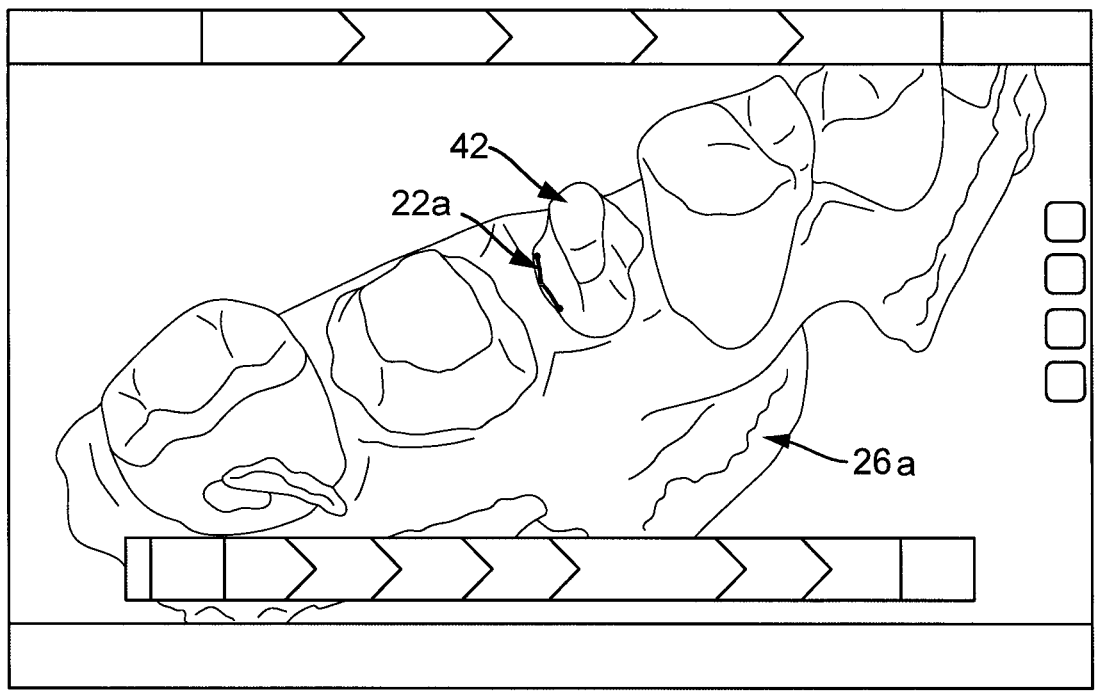
FIG. 4 illustrates a 3D model having a marginal line drawn around the base of a tooth (e.g., preparation/stump)
Figure 5:
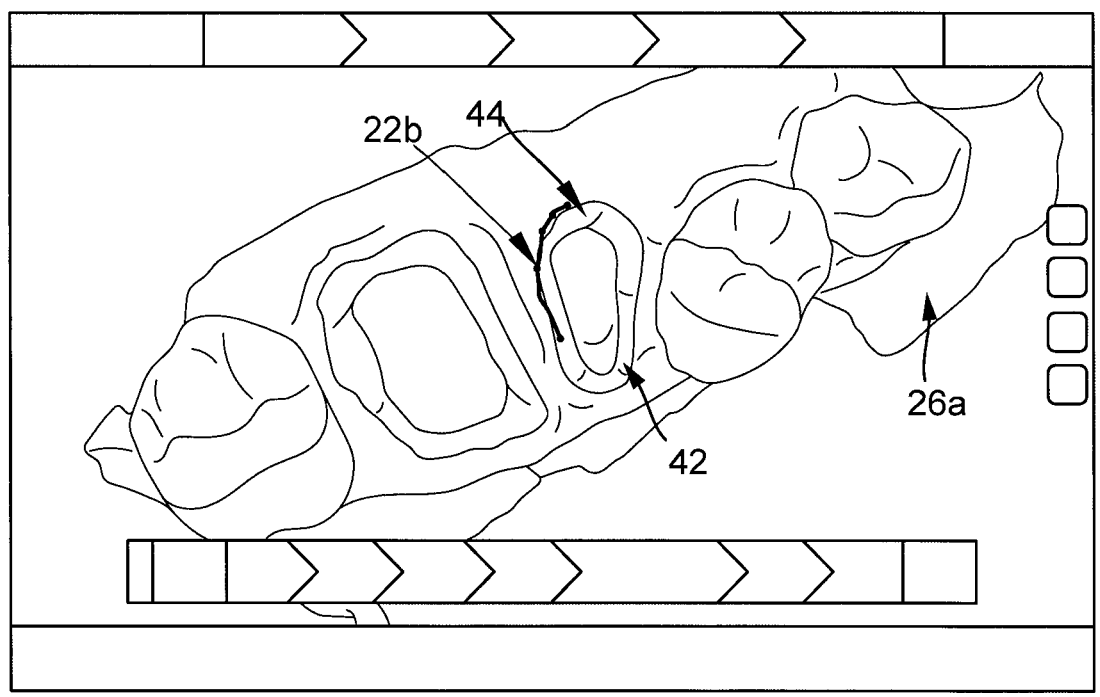
FIG. 5 illustrates the 3D model of FIG. 4 having a longer marginal line around the base of a tooth and a corresponding adjustment of the orientation of the 3D model.

In another exemplary embodiment herein, drawings such as lines, for example, a second marginal line 23 may be drawn on the 3D model 26. During the drawing of the second marginal line 23 the orientation/view direction on the 3D model 26 may continuously follow the surface normal of the current interaction point. Herein, during this adaptation/dynamic adjustment of the orientation, one or more surfaces 28 of the 3D model 26 may block a view of the surface being engaged. The one or more surfaces 28 preventing the direct view may then be for example, hidden, clipped or rendered transparent as shown in FIG. 3. In a further embodiment, the method may be applicable when using interaction tools 27 such as 3D CAD interaction elements including elements that allow (i) positioning of markers on the 3D model 26, (ii) deforming of a surface of the 3D model 26 (iii) movement or using of interaction elements which have a 3D correlation in position with respect to the 3D model's surface and whose correlation is changed by the user. Herein the model may be automatically rotated or zoomed, if the user moves the interaction elements over/along a surface of the 3D model 26, so that they are not moved to a side or backside of the 3D model 26 with respect to the view direction of the user. For example, FIG. 4 shows a 3D model 26a having a marginal line 22a drawn around the base of a tooth being prepared 42. As a user extends the marginal line 22a into an extended marginal line 22b, the orientation of the 3D model 26a may be changed from a first orientation as shown in FIG. 4 to a second orientation as shown in FIG. 5 such that a portion 44 of the dental anatomy is visible in or order to draw the extended marginal line 22b.

In another embodiment of the method, the adjustment of the view and/or orientation of the 3D model 26 may be done partially. Herein the adjustment may be done after a threshold is reached. The threshold may optionally be predetermined. The threshold may for example be based on (i) the magnitude of an angle between the surface normal and the view direction and/or (ii) size of a drawing (e.g. length of a drawn line) and/or (iii) accumulated covered curvature of the surface by a drawing. Similarly, a latency may be adopted such that dynamic adjustment occurs after the latency (such as an observed time period) is observed before adjusting in order to reduce or eliminate a "hopping" or erratic change in views. In an embodiment, a threshold value for the magnitude of the angle between the surface normal and the view direction may be, for example, an angle greater than 3° (for example and angle greater than 5°). In another embodiment, a threshold value for a length of a drawn line (eg. from a starting position to an current position) may be a length greater than 3 mm (for example a length greater than 5 mm). In another embodiment, a threshold value for the length of an accumulated curvature (eg. the curvature between a starting position and a current position) of a drawing/curve may be a length greater than 3 mm (eg. a length greater than 5 mm). In another embodiment, a threshold value for a latency value (eg. a time from the start of a drawing to a current time) may be a time greater than 0.5 s (eg. a time greater than is).

In yet another embodiment, dynamic adjustment may be initiated by a user. Herein the user may manually adjust the 3D model 26 until a command is given by the user to initiate the automatic, continuous and/or intermittent adjustment based on for example a threshold value of a drawing. In another embodiment, a drawing process may be paused as the dynamic adjustment occurs such that the drawing may not be completed off-course. Moreover, the dynamic adjustment may optionally be initiated after an ongoing drawing reaches a surface that is out of the user's view. In yet another exemplary embodiment a change of the orientation of the 3D model may be based on a pivot point wherein the pivot point is the last or current point being engaged by the user and wherein the 3D model is turned on that pivot point.

In another embodiment of the method, to avoid unsteady or flickering movements of the 3D model during dynamic adjustment, a threshold compensation smoothing calculation may be useful for the adjustment of the view/orientation wherein the threshold compensation smoothing calculation may relates to an accumulated curvature and/or distance on the 3D surface by a user drawing, so that the adjustments during the interaction with the 3D model may not lead to having the view tumble unnecessarily.

FIGS. 7-8 show example methods described herein comprising rendering a 3D model on a display in Step S10. A processor 13, 122 in tandem with a modeling system 16 may detect a user engagement or interaction process and may adjust the 3D model based on a detected localized area and the engagement process. For example, the processor 13, 122 may detect a single click or continuous move of an operator 25. The 3D model 26 may preferably remain unadjusted if processor 13, 122 detects a single click. If the processor 13, 122 detects a continuous movement of an operator 25, the processor may adjust the 3D model by for example rotating the 3D model as shown in Step S13. The adjustment may be based on an angle α between a view direction of the user 61 and a surface normal of the position of the operator 25, (such as a finger position on a surface of the 3D model 26 using a touchscreen display) exceeding a predetermined value x, Step S12. In another embodiment as shown in FIG. 8, the adjusting (e.g. rotation) of the 3D model may be continuous once the angle α exceeds the predetermined value x as in Step S14.

In view of the foregoing description, it may be appreciated that the example embodiments described herein provide a method and system for dynamically adjusting a view/orientation of the 3D model 26 based on a localized area of said 3D model 26. The method and system may be useful for reducing the number of times a user manually adjusts a view/orientation of the model during treatment planning.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A method for dynamically adjusting a 3D model, the method comprising steps of:
    engaging a 3D model on a screen, using a 3D model engagement process;
    identifying the 3D model engagement process;
    obtaining a localized area of the 3D model proximate to a location of the 3D model being engaged by defining a region of the 3D model proximate to the location of the 3D model being engaged, the localized area of the 3D model and the location of the 3D model being engaged are on the same screen and the 3D model is a dental 3D model;
    computing an orientation of the obtained localized area or location of the 3D model being engaged; and
    responsive to obtaining an obstructed view of a surface of the 3D model being engaged, adjusting the 3D model based on the orientation of the obtained localized area or location of the 3D model being engaged and the engagement process such that one or more surface normals or an average of surface normals of the localized area or location of the 3D model being engaged and a view direction coincide in order to produce an unobstructed or substantially unobstructed view of the surface the 3D model being engaged.

2. The method according to claim 1 wherein the adjusting step is automatic, continuous and/or intermittent.

3. The method according to claim 1, wherein the adjusting step includes (i) rotation of the 3D model, (ii) translation of the 3D model, (iii) magnification of the 3D model or a part of the model, (iv) making the 3D model or a part of the model transparent, and/or (v) coloring the 3D model or a part of the model.

4. The method according to claim 1, wherein the engagement process includes deforming/modifying the surface of the 3D model being engaged.

5. The method according to claim 1, wherein the adjusting step is further based on a predetermined threshold value of said angle.

6. The method according to claim 1, wherein the adjusting step includes a context awareness step wherein an extent of the adjusting is based on properties of the 3D model.

7. The method according to claim 6, wherein the properties include tooth structure and/or tooth shape.

8. The method according to claim 1, wherein the engagement process is a continuous movement of an operator.

9. A system for dynamically adjusting a 3D model, the system comprising:
    at least one processor configured to:
        identify a 3D model engagement process;
        obtain a localized area of the 3D model proximate to a location of the 3D model being engaged by defining a region of the 3D model proximate to the location of the 3D model being engaged, the localized area of the 3D model and the location of the 3D model being engaged are on the same screen and wherein the 3D model is a dental 3D model,
        compute an orientation of the obtained localized area or location of the 3D model being engaged; and
        responsive to obtaining an obstructed view of a surface of the 3D model being engaged, adjust the 3D model based on the orientation of the obtained localized area or location of the 3D model being engaged, and the engagement process such that one or more surface normals or an average of surface normals of the localized area and a view direction coincide in order to produce an unobstructed or substantially unobstructed view of the surface of the 3D model being engaged.

10. The system according to claim 9 wherein the adjusting is automatic, continuous and/or intermittent.

11. The system according to claim 9, wherein the adjusting steps includes (i) rotation of the 3D model, (ii) translation of the 3D model, (iii) magnification of the 3D model or a part of the model, (iv) making the 3D model or a part of the model transparent and/or (v) coloring the 3D model or a part of the model.

12. The system according to claim 9, wherein the engagement process includes deforming the surface of the 3D model being engaged.

13. The system according to claim 9, wherein the adjusting is further based on a predetermined threshold value of said angle.

14. The system according to claim 9, wherein the adjusting includes a context awareness step wherein an extent of the adjusting, is based on properties of the 3D model.

15. A method for dynamically adjusting a dental 3D model, the method comprising steps of:
engaging a 3D model on a screen using a 3D model engagement process, by continuously deforming/modifying a surface of the 3D model along a plurality of locations of the 3D model;
identifying the 3D model engagement process;
continuously obtaining, during the continuously deforming/modifying step, for each location of the plurality of locations of the 3D model being engaged, a localized area of the 3D model proximate to said location by defining a region of the 3D model proximate to the location of the 3D model being engaged, the localized area of the 3D model and said location are on the same screen; and
responsive to obtaining an obstructed view of the surface of the 3D model being engaged, continuously adjusting the 3D model during the continuously deforming/modifying step, for each location of the plurality of locations of the 3D model being engaged, based on the orientation of the obtained localized area or location of the 3D model being engaged and the engagement process such that an angle formed by (i) one or more surface normals or an average of surface normals of the localized area or location of the 3D model being engaged and (ii) a view direction exceeds a predetermined threshold value, the view direction is updated to follow said one or more surface normals or the average of surface normals of the localized area during the continuously deforming/modifying step.

16. A method for dynamically adjusting a dental 3D model, the method comprising the steps of:
engaging a 3D model on a screen using a 3D model engagement process, by continuously deforming/modifying a surface of the 3D model along a plurality of locations of the 3D model;
identifying the 3D model engagement process;
continuously obtaining, during the continuously deforming/modifying step, for each location of the plurality of locations of the 3D model being engaged, a localized area of the 3D model proximate to said location by defining a region of the 3D model proximate to the location of the 3D model being engaged, the localized area of the 3D model and said location are on the same screen; and
responsive to obtaining an obstructed view of the surface of the 3D model being engaged, continuously adjusting the 3D model during the continuously deforming/modifying step, for each location of the plurality of locations of the 3D model being engaged, the 3D model based on an orientation of the obtained localized area or location of the 3D model being engaged,
wherein the continuously adjusting, which occurs during the continuously deforming/modifying step includes magnification of the 3D model or a part of the model and/or coloring.

\* \* \* \* \*